(12) United States Patent
Frick et al.

(10) Patent No.: US 7,019,023 B2
(45) Date of Patent: Mar. 28, 2006

(54) BENZOTHIEPINE 1, 1-DIOXIDE DERIVATIVES, A PROCESS FOR THEIR PREPARATION, PHARMACEUTICALS COMPRISING THESE COMPOUNDS, AND THEIR USE

(75) Inventors: Wendelin Frick, Hünstetten-Beuerbach (DE); Alfons Enhsen, Büttelborn (DE); Heiner Glombik, Hofheim (DE); Hubert Heuer, Schwabenheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 69 days.

(21) Appl. No.: 10/606,771

(22) Filed: Jun. 27, 2003

(65) Prior Publication Data

US 2004/0087648 A1 May 6, 2004

Related U.S. Application Data

(63) Continuation of application No. 10/201,050, filed on Jul. 24, 2002, now Pat. No. 6,642,269, which is a continuation of application No. 09/773,772, filed on Feb. 2, 2001, now Pat. No. 6,441,022, which is a continuation of application No. 09/398,315, filed on Sep. 20, 1999, now Pat. No. 6,221,897, which is a continuation of application No. PCT/EP99/03743, filed on May 29, 1999.

(30) Foreign Application Priority Data

Jun. 10, 1998 (DE) ................................ 198 25 804

(51) Int. Cl.
*A61K 31/38* (2006.01)
(52) U.S. Cl. ................................... 514/431
(58) Field of Classification Search ................. 514/431
See application file for complete search history.

(56) References Cited

U.S. PATENT DOCUMENTS

| | | |
|---|---|---|
| 3,287,370 A | 11/1966 | Mohrbacher et al. |
| 3,389,144 A | 6/1968 | Mohrbacher et al. |
| 3,520,891 A | 7/1970 | Mohrbacher et al. |
| 3,694,446 A | 9/1972 | Houlihan et al. |
| 3,758,528 A | 9/1973 | Malen et al. |
| 3,770,728 A | 11/1973 | Bourquin et al. |
| 3,821,249 A | 6/1974 | Malen et al. |
| 3,853,915 A | 12/1974 | Bourquin et al. |
| 3,928,383 A | 12/1975 | Kaplan et al. |
| 3,954,764 A | 5/1976 | Gerecke et al. |
| 4,044,010 A | 8/1977 | Gerecke et al. |
| 4,045,570 A | 8/1977 | Dörhöfer et al. |
| 4,153,612 A | 5/1979 | McCall |
| 4,185,109 A | 1/1980 | Rosen |
| 4,207,239 A | 6/1980 | McCall |
| 4,237,296 A | 12/1980 | Gadient |
| 4,247,553 A | 1/1981 | McCall |
| 4,251,526 A | 2/1981 | McCall |
| 4,436,749 A | 3/1984 | Hatinguais et al. |
| 5,037,825 A | 8/1991 | Klaus et al. |
| 5,158,943 A | 10/1992 | Sohda et al. |
| 5,164,387 A | 11/1992 | Klaus et al. |
| 5,169,857 A | 12/1992 | Angerbauer et al. |
| 5,300,522 A | 4/1994 | Klaus et al. |
| 5,420,273 A | 5/1995 | Klaus et al. |
| 5,430,116 A | 7/1995 | Kramer et al. |
| 5,491,152 A | 2/1996 | Wilde et al. |
| 5,547,975 A | 8/1996 | Talley et al. |
| 5,594,001 A | 1/1997 | Teleha et al. |
| 5,602,152 A | 2/1997 | Berthelone et al. |
| 5,652,252 A | 7/1997 | Berthelone et al. |
| 5,670,532 A | 9/1997 | Talley et al. |
| 5,886,016 A | 3/1999 | Talley et al. |
| 5,994,391 A | 11/1999 | Lee et al. |

(Continued)

FOREIGN PATENT DOCUMENTS

DE 2011806 10/1970

(Continued)

OTHER PUBLICATIONS

Ali, M., et al., "Reactions with 2,3,4,5-Tetrahydro-benzo (B) Thiepin-5-One and Its Derivatives," *J. Prakt. Chem.* 316(2): 259-266(1974).

(Continued)

*Primary Examiner*—Deborah C. Lambkin
(74) *Attorney, Agent, or Firm*—Finnegan, Henderson, Farabow, Garrett and Dunner, L.L.P.

(57) ABSTRACT

Substituted benzothiepine 1,1-dioxide derivatives of formula I:

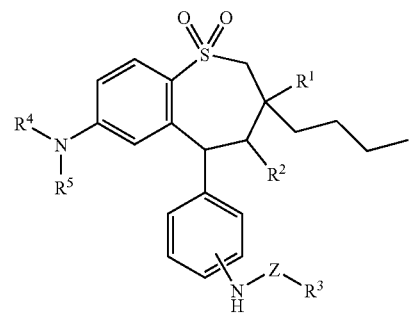

in which $R^1$, $R^2$, $R^3$, $R^4$, $R^5$ and Z have the meanings indicated, and their physiologically tolerable salts and physiologically functional derivatives and a process for their preparation are described. The compounds are suitable, for example, as hypolipidemics.

10 Claims, No Drawings

U.S. PATENT DOCUMENTS

| | | | |
|---|---|---|---|
| 5,998,400 | A | 12/1999 | Brieaddy et al. |
| 6,013,809 | A | 1/2000 | Zimmer et al. |
| 6,083,977 | A | 7/2000 | Boehm et al. |
| 6,107,494 | A | 8/2000 | Lee et al. |
| 6,143,755 | A | 11/2000 | Bocan |
| 6,180,660 | B1 | 1/2001 | Whitney et al. |
| 6,221,897 | B1 | 4/2001 | Frick et al. |
| 6,235,771 | B1 | 5/2001 | Shiraishi et al. |
| 6,262,277 | B1 | 7/2001 | Lee et al. |
| 6,268,392 | B1 | 7/2001 | Keller et al. |
| 6,277,831 | B1 | 8/2001 | Frick et al. |
| 6,369,220 | B1 | 4/2002 | Li et al. |
| 6,387,924 | B1 | 5/2002 | Lee et al. |
| 6,387,944 | B1 | 5/2002 | Frick et al. |
| 6,420,417 | B1 | 7/2002 | Keller et al. |
| 6,441,022 | B1 | 8/2002 | Frick et al. |
| 2002/0032329 | A1 | 3/2002 | Babiak et al. |
| 2002/0061888 | A1 | 5/2002 | Keller et al. |
| 2003/0017996 | A1 | 1/2003 | Frick et al. |

FOREIGN PATENT DOCUMENTS

| | | |
|---|---|---|
| EP | 0067086 | 12/1982 |
| EP | 0250265 | 12/1987 |
| EP | 0350846 | 1/1990 |
| EP | 0508425 | 10/1992 |
| EP | 0781278 | 7/1997 |
| EP | 0791592 | 8/1997 |
| EP | 0922703 | 6/1999 |
| FR | 2661676 | 11/1991 |
| FR | 2698873 | 6/1994 |
| GB | 1211258 | 11/1970 |
| GB | 1428110 | 3/1976 |
| SU | 506297 | 3/1976 |
| SU | 550982 | 3/1977 |
| SU | 591146 | 1/1978 |
| WO | WO 93/16055 | 8/1993 |
| WO | WO 96/08484 | 3/1996 |
| WO | WO 96/16051 | 5/1996 |
| WO | WO 97/33882 | 9/1997 |
| WO | WO 98/38182 | 9/1998 |
| WO | WO 98/40375 | 9/1998 |
| WO | WO 98/55118 | 12/1998 |
| WO | WO 99/32478 | 7/1999 |
| WO | WO 00/01687 | 1/2000 |
| WO | WO 00/38725 | 7/2000 |
| WO | WO 01/68637 | 9/2001 |
| WO | WO 02/08211 | 1/2002 |

OTHER PUBLICATIONS

Almena J. et al, "Reductive Opening of Thiophthalan: A New Route to Functionalised Sulfur-Containing Compounds.", J. Org. Chem., vol. 61, pp. 1859-1862, 1996.

Baumgarth M. et al, "Bicyclic Acylguanidine $Na^+/H^+$ Antiporte Inhibitors", J. Med. Chem. vol. 41, pp. 3736-3747, 1998.

Bentley, K. W. et al., "Pharmaceutical Antihypertensive and Vasodilator Compositions", Chemical Abstracts, vol. 85, p. 516, (1976).

Berthelon et al., "Benzoxepinopyridine derivatives," Chemical Abstracts, vol. 121, p. 1161 (1994).

Bohme, H. and Haack, B., "[Derivatives of 1,3,4,5-tetrahydro-2-benzothiepin with a basic side chain in the 1-position]," Arch. Pharm. Ber. Dtsch. Pharm. Ges. 302(1): 72-74 (1969).

Braun et al. "2,3,4,5,6-Penta-O-Acetyl-D-Gluconic Acid and 2,3,4,5,6-Penta-O-Acetyl-D-Gluconyl Chloride," Organic Synthesis, vol. 5, pp. 887-891 (1973).

Chatterjee, A., et al., "Ring contraction of some 1-benzothiepin derivatives to 1-benzothiophens," J. Chem. Soc. Perkin Trans. 1:1707-1711 (1981).

Corelli F. et al., "Diltiazem-like Calcium Entry Blockers: A Hypothesis of the Receptor-Binding Site Based on a Comparative Molecular Field Analysis Model.", J. Med. Chem., vol. 40, pp. 125-131, 1997.

Deshayes C. et al. "Synthesis of some 4-Acetyl-3,5-dioxo-2,3,4-tetrahydro[1]benzoxepine or Benzothiepine and 6-Acetyl-5,7-dioxo-6,7,8,9-tetrahydor-5H-benzocycloheptene Derivatives", J. Heterocyclic Chem., vol. 22, No. 6, pp. 1659-1662, (1985).

Ferrari, R., et al., "How do calcium antagonists differ in clinical practice?," Cardiovascular drugs and therapy 8: 565-575 (1994).

Hofmann, H. and Dickert, F., "The dynamic behaviour of the 1-methyl-1-benzothiepinium ring system," Z. Natuforsch. B Anorg. Chem. Org. Chem. 36(8):974-977 (1981).

Hofmann, H. and Djafari, H., "Heterocyclic seven-membered ring compounds, xxxiv. A simple synthesis of 1-benzoxepine and 1-benzothiepine," Z. Natuforsch. B 44 (2):220-224 (1989).

Hofmann, H. and Djafari, H., "Heterocyclic seven-membered ring compounds, xxviii.—on 5-acetoxy-and 5-methoxy-1-benzothiepine and analogous 1-benzoxepines," Liebigs Ann. Chem. 3:599-604 (1985).

Hofmann, H. and Djafari, H., "Heterocyclic seven-membered ring compounds, xxxi.—the photochemical behaviour of monosubstituted 1-benzothiepines," Liebigs Ann. Chem.505-508 (1987).

Hofmann, H. and Heidrich, R., "Heterocyclic seven-membered ring compounds, xxiv. Photochemical reaction of 2-methyl-4-phenyl-1-benzothiepins," Z. Naturforsch. B. Anorg. Chem. Org. Chem. 37(10):1344-1345 (1982).

Hofmann, H. and Heidrich, R., "Heterocyclic Seven-Membered Ring Compounds XXIII. Synthesis and Thermolytic Behavior of 2-Methyl-4-Phenyl-1-benzothiepins" Z. Naturforsch. B 34(8):1145-1148 (1979).

Hofmann, H. and Loew, G., "Heterocyclic seven-membered ring compounds, xxvii. Synthesis and thermal reactivity of 1,2-dimethyl-4-phenyl-1-benzothiepinium salts," Z. Naturforsch. B Anorg. Chem. Org. Chem. 39(7):985-989 (1984)

Hofmann, H., et al., "Heterocyclic seven-membered ring compounds, xxv—synthesis and thermolysis of substituted 1-methyl-4-phenyl-1-benzothiepinium salts," Liebigs Ann. Chem. 3:425-432 (1983).

Hofmann, H., et al., "Synthesis of stable 1-benzothiepins," Angew Chem. Int. Ed. Engl. 11(5): 423-424 (1972).

Huckle et al., "4-Amino-2,3,4,5-tetrahydro-1-benzoxepin-5-ols, 4-Amino-2,3,4,5-tetrahydro-1-benzothiepin-5-ols and related compounds," J. Chem. Soc. C 12:2252-2260 (1971).

Ishino Y. et al., "Novel Synthesis of 4,5-Bis(arylthio)-2,3,4,5-tetrahydro-1-benzothiepins: Noteworthy Cyclization by the Reaction of 2-Butynedion with Arenethiols in the Presence of Zinc Iodide.", Communications, pp. 827-829, 1987.

Jilek J. et al., "8-Chloro and 8-Methylthio Derivatives of 10-Piperazino-10,11-DiHydrodisenzo[b,f]Thiepins; New Compounds and New Procedures", Neurotropic and Psychotropic Agents: Part CLXXVII, Journal 48, pp. 906-927, (1983).

Journal Bioorganicheskaya khimiya, (Bioorganic chemistry), Publisher Nauka, Academy of Sciences of the USSR, v. 9, No 10, 1983, pp. 1357-1358 and partial translation.

Journal of organic chemistry, Publisher Nauka, Russian Academy of Sciences, v. 34, issue 3, p. 324, 1998 and partial translation.

Khimiko-farmatsevticheskij zhurnal, (Chemical—and—pharmaceutical journal), 1984, v. XVIII, No. 9, pp. 1105-1110, and partial translation.

Khimiko-farmatsevticheskij zhurnal, (Chemical—and—pharmaceutical journal), Moscow, Meditsina, Ministry of medical industry of the USSR, monthly science-engineering and production journal, 1985, v. XIX, No 9, pp. 1080-1086 and parital translation.

Khimiko-farmatsevticheskij zhurnal, (Chemical—and—pharmaceutical journal), Moscow, Meditsina, Ministry of medical industry of the USSR, monthly science-engineering and production journal, 1985, v. XIX, No. 9, pp. 1057-1060 and partial translation.

Khimiko-farmatsevticheskij zhurnal, (Chemical—and—pharmaceutical journal), Moscow, Meditsina, Minisitry of medical industry of the USSR, monthly science-engineering and production journal, 1982, v. XVI, No 2, pp. 173-176 and partial translation.

Khimiko-farmatsevticheskij zhurnal, (Chemical—and—phamaceutical journal), Moscow, Meditsina, Ministry of medical and microbiological industry of the USSR, 1988, No 8, and partial translation.

Kramer W. et al., "Bile Acid Derived HMG-CoA reductase inhibitors", Biochimica et Biophysica Acta 1227, pp. 137-154, (1994).

Kvis F. et al., "Benzocycloheptenes and Heterocyclic Ananlogues as Potential Drugs. VII. 4-Phenyl-2,3,4,5-Tetrahydro-1-Benzothiepins and some related compounds.", Collection Czechoslov. Chem. Comm., vol. 37, pp. 3808-3816, 1972.

Lenz G.R., "The Synthesis of the Isoquinoline Alkaloid Calycotomine via Functionalization of Enamide Double Bonds", Department of Medical Chemistry, G.D. Searle & Company, Heterocylces, vol. 26, No. 3, pp. 721-730, (1987).

Menozzi G. et al., "Reaction of Ketenes with Heterocyclic N,N-Disubstituted α-Aminomethyleneketones. XVII. Synthesis of 2H- [1]Benzothiepino[5,4-b]pyran Derivatives", J. Heterocylcic Chem. vol. 23, pp. 449-454, (1986).

Menozzi G. et al., "Reaction of Sulfenes with Heterocyclic N,N-Disubstituted α-Aminomethyleneketones. XII. Synthesis of [1]Benzothiepino[5,4-e] [1,2]oxathiin Derivatives", J. Heterocylcic Chem. vol. 23, pp. 455-458, (1986).

Murata, I., "Some new aspects of thiepine and thiazepine chemistry," *Phosphorus, Sulfur Silicon Relat. Elem.* 43(3-4):243-260 (1989).

Nakao, S. et al., "4-(Aminomethyl)-2,3-dihydri-1-benzothiepins as Cardiovascular Agents", Chemical Abstracts, vol. 114, p. 825, (1991).

Nakao S. et al, Studies on the Synthesis of Condensed Pyridazine Derivatives. IV. Synthesis and Anxiolytic Activity of 2-Aryl-5,6-dihydro—(1)Benzothiepino[5,4-c]pyridazin-3(2H)-ones and Related Compound, Chem. Pharm. Bull. vol. 39 No. 10, 2556-2563, (1991).

Nagamatsu T. et al, "Polycyclic N-Hetero Compounds. XXXVII. A Convenient Synthesis and Evaluation of Antiplatelet Aggregation Activity of 1,2,4,5-Tetrahydro[1]-benzothiepino[5,4-e]imidazo[1,2-c]pyrimidine and its Related Compounds.", Journal of Heterocyclic Chemistry, vol. 28, pp. 513-515, 1991.

Oda T. et al., "Synthesis of Novel 2-Benzothiopyran and 3-Benzothiepin Derivatives and Their Stimulatory Effect on Bone Formation", J. Med. Chem., vol. 42, pp. 751-760, 1999.

Patra R., et al., "Conformational and Steric Requirements of the Side Chain for Sulphur Participation in Benzothiepin Derivatives", Tetrahedron Letters, vol. 30, pp. 4279-4282, 1989.

Protiva, M., "Neurotropic and psychotropic drugs," *Pharm. Ind.* 32(10A):923-935 (1970).

Pye C. et al., "Examination of the Valence Tautomers Benzene Oxide and Oxepin and Two Derivative Systems by *ab Initio* Methods", J. Phys. Chem. A, pp. 3371-3376, (1997).

Rehse, K. and Bienfait, R., "Anticoagulante eigenschaften heterocyclischer 1,3-diketone [Anticoagulant activities of heterocyclic 1,3-diones]," *Archiv. der Pharmazie* (*Weinheim*) 317(5):385-393 (1984).

Ricci A., et al., "New heterocyclic systems, IV. Derivatives of (1) Benzothiepine," *Gazz. Chim. Ital.* 107(1-2):19-26 (1977).

Shafiee A. et al., "Chemistry of 1,2,3,-Thiadiazole. IV. Synthesis of [1]Benzoxepino- [ 3,4-d][1,2,3] thiadiazole, [1] Benzothiepino-[ 3,4-d][1,2,3]thiadiazole, [1]Benzoxepino[ 4,3-d ]oxazole and [ 1]Benzoxepino[3,4-d]oxazole. Four Novel Heterocycles", J. Heterocyclic Chem. vol. 18, pp. 899-903. (1981).

Sindelar K. et al., "Dibenzo[b,f]Thiepin-10-Carbonitrile, ITS 10,11-Hydro Derivate Some Transformation Products and Related Compounds", Neurotropic and Psychotropic Agents, Part CLXXX, Journal 48, 1173, pp. 1187-1211, (1983).

Sindelar K. et al., "Benzocycloheptenes and Heterocyclic Analogues as Potential Drugs. III. Further Synthetic Experiments in the Series of 1-Benzothiepin Derivatives.", Collection Czechoslov. Chem. Comm., vol. 37, pp. 1195-1206, 1972.

Sindelar K. et al., "Neurotropic and Psychotropic Compounds. XXIX. Derivatives of 2,3,4,5-Tetrahydro-1-Benzothiepin.", Collection Czechoslov. Chem. Commun., vol. 33, pp. 4315-4327, 1968.

Solladie G. et al., "A New Family of Enantiomerically Pure Smectic C * Liquid Crystals with a Bridged Chiral Biphenyl Core.", J. Org. Chem., vol. 63, pp. 3895-3898, 1998.

Takada T., "Oxidatie Biaryl Coupling Reaction of Phenol Ether Derivatives Using a Hypervalent Iodine (III) Reagent.", J. Org. Chem., vol. 63, pp. 7698-7706, 1998.

Talley J.J., "Discovery of the COX-2 inhibitor Celebrex", Nippon Yakugakkai Nenka I Koen Yoshishu, vol. 120, No. 1, p. 80 (2000).

Tamura Y et al., "Rearrangement of 4-Oxothiochroman-1-io(bismethoxycarbonyl)methanides to Tetrahydro-1-Benzothiepin-5-ones", J.C.S. Perkin I, pp. 2978-2981, (1981).

Traynelis, V., et al., "Seven-Membered Heterocycles, III. Homoallylic Resonance and a Unique Sulfur Extrusion Reaction in Seven-Membered Sulfur Hetercycles", vol. 29, pp. 1092-1097, (1964).

Traynelis V., et al., "Seven-membered heterocycles, viii. 1-benzothiepin sulfoxides and a convenient synthesis of sulfoxides," *J. Org. Chem.* 38(23):3986-3990 (1973).

Traynelis, V., et al., "Seven-membered heterocycles, ix. Synthesis and properties of some 5-alkyl and -aryl derivatives of 1-benzothiepin," *J. Org. Chem.,* 43(17):3379-3384 (1978).

Traynelis, V., et al., "Seven-membered heterocycles, vii. The synthesis and properties of 1-benzothiepin and its chlorinated derivatives," *J. Org. Chem.* 38(23):3978-3986 (1973).

Traynelis, V., et al., "Seven-Membered Heterocycles VI. 4-Alkylidene-1-Benzothiepin-(2H)-ones and the Reaction of Halogenated 3,4-Dihydro-1-Benzotheipin—5 (2H)-ones with Base[1-3]", J. Org. Chem., vol. 38, No. 15, pp. 2629-2637, (1973).

Vejdelek, Z. and Protiva, M., "Synthetic experiments aiming at 1,2,4,5-tetrahydro-3-benzothiepin derivatives," *Collect. Czech. Chem. Commun.* 55(9):2351-2356 (1990).

Viou, F., Thesis, Syntheses d'heterocycles derives du disubstitue-3,4-benzenethiol a potentialite anti-allergique [Synthesis of heterocycles derived from 3,4-disubstituted benzenethiol, potent antiallergics,] Montpellier Univ., France (1986).

Wess G. et al., "Synthesis and Biological Activity of Bile Acid-Derived HMG-CoA Reductase Inhibitors. The Role of 21-Methyl in Recognition of HMG-CoA Reductase and the Ileal Bile Acid Transport System", J. Med. Chem., pp. 3240-3246, (1994).

Derwent Abstract of FR 2,661,676.
Derwent Abstract of FR 2 698 873.
Derwent Abstract of DE 2011806.
Derwent Abstract of SU 550982.
Derwent Abstract of SU 506297.
Derwent Abstract of SU 591146.
Derwent Abstract of EP 67086.
Derwent Abstract of EP 350846.
Derwent Abstract of EP 922703.

BENZOTHIEPINE 1,1-DIOXIDE DERIVATIVES, A PROCESS FOR THEIR PREPARATION, PHARMACEUTICALS COMPRISING THESE COMPOUNDS, AND THEIR USE

This application is a continuation of application Ser. No. 10/201,050, filed on Jul. 24, 2002, now U.S. Pat. No. 6,642,268 which is a continuation of application Ser. No. 09/773,772, filed Feb. 2, 2001, now U.S. Pat. No. 6,441,022 which is a continuation of application Ser. No. 09/398,315, filed Sep. 20, 1999, now U.S. Pat. No. 6,221,897 which a continuation of International Application No. PCT/EP99/03743, filed May 29, 1999, all of which are incorporated herein by reference.

The invention relates to substituted benzothiepine 1,1-dioxide derivatives, their physiologically tolerable salts and physiologically functional derivatives.

The present application is a continuation of PCT application PCT/EP99/03743, which designates the United States, and was filed May 29, 1999. The present application and the PCT application claim priority to German patent No. 19825804.6, filed Jun. 10, 1998, and issued Apr. 16, 1999. Both prior applications are entirely incorporated by reference herein.

Benzothiepine 1,1-dioxide derivatives and their use for the treatment of hyperlipidemia as well as arteriosclerosis and hypercholesterolemia have already been described. PCT Application No. PCT/US97/04076, publication No. WO 97/33882. The disclosure of that publication is entirely incorporated by reference herein.

One object of the present invention is the improved availability of compounds which display a therapeutically utilizable hypolipidemia action. In particular, novel compounds satisfy this object when they bring about the same magnitude of fecal bile acid excretion at a significantly lower dosage than that required of currently-known compounds. A dose reduction of the $ED_{200}$ value by at least a factor of 5 compared with the compounds currently known is particularly desirable. The present invention unexepectedly satisfies this object.

The invention therefore relates to compounds of formula I:

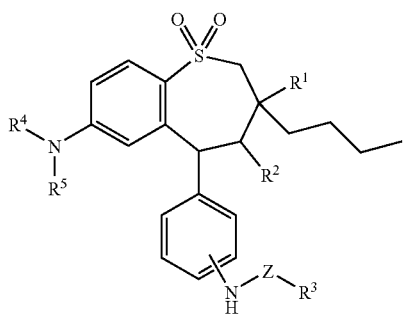

I in which
$R^1$ is methyl, ethyl, propyl, or butyl;
$R^2$ is H, OH, $NH_2$, or $NH—(C_1–C_6)$-alkyl;
$R^3$ is a sugar radical, a disugar radical, a trisugar radical, or a tetrasugar radical, wherein said radicals are optionally mono- or polysubstituted by a sugar protective group;
$R^4$ is methyl, ethyl, propyl, or butyl;
$R^5$ is methyl, ethyl, propyl, or butyl;
Z is $—(C=O)_n—(C_0–C_{16})$-alkyl-, $—(C=O)_n—(C_0–C_{16})$-alkyl-NH—, $—(C=O)_n—(C_0–C_{16})$-alkyl-O—, $—(C=O)_n—(C_1–C_{16})$-alkyl-$(C=O)_m$, or a covalent bond;
n is 0 or 1;
m is 0 or 1;

and their pharmaceutically tolerable salts and physiologically functional derivatives.

Preferred compounds of formula I are those in which one or more radicals have the following meaning:
$R^1$ is ethyl, propyl, or butyl;
$R^2$ is H, OH, $NH_2$, or $NH—(C_1–C_6)$-alkyl;
$R^3$ is a sugar radical, or disugar radical, wherein said radicals are optionally mono- or polysubstituted by a sugar protective group;
$R^4$ is methyl, ethyl, propyl, or butyl;
$R^5$ is methyl, ethyl, propyl, or butyl;
Z is $—(C=O)_n—(C_0–C_{16})$-alkyl-, $—(C=O)_n—(C_0–C_{16})$-alkyl-NH—, $—(C=O)_n—(C_0–C_{16})$-alkyl-O—, $—(C=O)_n—(C_1–C_{16})$-alkyl-$(C=O)_m$, or a covalent bond;
n is 0 or 1;
m is 0 or 1;

and their pharmaceutically tolerable salts.

Particularly preferred compounds of formula I are those in which one or more radicals have the following meaning:
$R^1$ is ethyl or butyl;
$R^2$ is OH;
$R^3$ is a sugar radical, wherein the sugar radical is optionally mono- or polysubstituted by a sugar protective group;
$R^4$ is methyl;
$R^5$ is methyl;
Z is $—(C=O)—(C_0–C_4)$-alkyl, or a covalent bond;

and their pharmaceutically tolerable salts.

On account of their higher water solubility compared with the starting or base compounds, pharmaceutically tolerable salts are particularly suitable for medicinal applications. These salts must have a pharmaceutically tolerable anion or cation. Suitable pharmaceutically tolerable acid addition salts of the compounds according to the invention are salts of inorganic acids, such as hydrochloric acid, hydrobromic, phosphoric, metaphosphoric, nitric, sulfonic and sulfuric acid, and of organic acids, such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acid. For medicinal purposes, the chlorine salt is particularly preferably used. Suitable pharmaceutically tolerable basic salts are ammonium salts, alkali metal salts (such as sodium and potassium salts) and alkaline earth metal salts (such as magnesium and calcium salts).

Salts with an anion or cation which is not pharmaceutically tolerable are likewise included in the scope of the invention as useful intermediates for the preparation or purification of pharmaceutically-tolerable salts and/or for use in nontherapeutic, for example in-vitro, applications.

The term "physiologically functional derivative" used here indicates any physiologically tolerable derivative of a compound according to the invention, e.g. an ester which, on administration to a mammal, such as, for example, man, is able to form, directly or indirectly, such a compound or an active metabolite thereof.

A further aspect of this invention are prodrugs of the compounds according to the invention. Such prodrugs can be metabolized in vivo to give a compound according to the invention. These prodrugs can themselves be active or inactive.

The compounds according to the invention can also be present in various polymorphic forms, e.g. as amorphous and crystalline polymorphic forms. All polymorphic forms of the compounds according to the invention are included in the scope of the invention and are a further aspect of the invention.

Below, all references to "compound(s) according to formula I" refer to compound(s) of formula I as described above, and also their salts, solvates and physiologically functional derivatives as described herein.

The compounds of formula I and their pharmaceutically tolerable salts and physiologically functional derivatives are ideal pharmaceuticals for the prophylaxis and treatment of lipid metabolism disorders, in particular of hyperlipidemia. The compounds of formula I are likewise suitable for influencing, in particular, lowering, the serum cholesterol level and for the prophylaxis and treatment of one or more arteriosclerotic symptoms. When these compounds are used for prophylaxis, one skilled in the art has many means to determine or predict a patient's need for such prophylaxis. These methods are well-known in the art. The compounds can optionally also be administered in combination with statins, such as, for example, simvastatin, fluvastatin, pravastatin, cerivastatin, lovastatin or atorvastatin.

The compounds according to the invention are also suitable for the prophylaxis or treatment of gallstones.

The amount of a compound according to formula I which is necessary in order to achieve the desired biological effect is dependent on a number of factors, e.g. the specific compound selected, the intended use, in particular whether for prophylaxis or for treatment, the manner of administration and the clinical condition of the patient. In general, the daily dose is in the range from 0.1 mg to 100 mg (typically from 0.1 mg to 50 mg) per day per kilogram of body weight, e.g. 0.1–10 mg/kg/day. Tablets or capsules can contain, for example, from 0.01 to 100 mg, typically from 0.02 to 50 mg. In the case of pharmaceutically tolerable salts, the abovementioned weight data relate to the weight of the benzothiepine ion derived from the salt. For the prophylaxis or therapy of the abovementioned conditions, the compounds according to formula I can be used themselves as the compound, but preferably they are present in the form of a pharmaceutical composition with at least one pharmacologically tolerable excipient. The excipient must of course be tolerable in the sense that it is compatible with the other constituents of the composition and is not harmful to the health of the patient. The excipient can be a solid or a liquid or both and is preferably formulated with the compound as an individual dose, for example as a tablet, which can contain from 0.05% to 95% by weight of the compound of formula I. Further pharmaceutically active substances can also be present, including further compounds according to formula I. The pharmaceutical compositions according to the invention can be prepared by one of the known pharmaceutical methods, which essentially consists in mixing the constituents with pharmacologically tolerable excipients and/or auxiliaries.

Pharmaceutical compositions according to the invention are those which are suitable for oral and peroral (e.g. sublingual) administration, although the most suitable manner of administration is dependent in each individual case on the nature and severity of the condition to be treated and on the type of the compound according to formula (I) used in each case. Coated formulations and coated delayed-release formulations are also included in the scope of the invention. Acid-resistant and enteric formulations are preferred. Suitable enteric coatings include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration can be present in separate units, such as, for example, capsules, cachets, lozenges or tablets, which in each case contain a specific amount of the compound according to formula (I); as a powder or granules; as a solution or suspension in an aqueous or nonaqueous liquid; or as an oil-in-water or water-in-oil emulsion. As already mentioned, these compositions can be prepared according to any suitable pharmaceutical method which includes a step in which the active compound and the excipient (which can consist of one or more additional constituents) are brought into contact. In general, the compositions are prepared by uniform and homogeneous mixing of the active compound with a liquid and/or finely divided solid excipient, after which the product, if necessary, is shaped. For example, a tablet can thus be prepared by pressing or shaping a powder or granules of the compound, if appropriate with one or more additional constituents. Pressed tablets can be produced by tableting the compound in free-flowing form, such as, for example, a powder or granules, if appropriate mixed with a binder, lubricant, inert diluent and/or one or more surface-active agents and/or one or more dispersing agents in a suitable machine. Shaped tablets can be produced by shaping the compound in powder form moistened with an inert liquid diluent in a suitable machine.

Pharmaceutical compositions which are suitable for peroral (sublingual) administration include lozenges which contain a compound according to formula (I) with a flavoring, customarily sucrose and gum arabic or tragacanth, and pastilles which include the compound in an inert base such as gelatin and glycerol or sucrose and gum arabic.

The invention furthermore relates both to isomer mixtures of formula I, and the pure stereoisomers of formula I, as well as diastereomer mixtures of formula I and the pure diastereomers. Resolution of enantiomerically pure compounds is performed by methods well-known in the art. For example, a chiral acid or base can be added to a racemic or diastereomer mixture, and separation is then performed chromatographically. Another possible method uses a chirally selective chromatography column to resolve the mixture.

Preferred-racemates and enantiomerically pure compounds of formula I are those having the following structure:

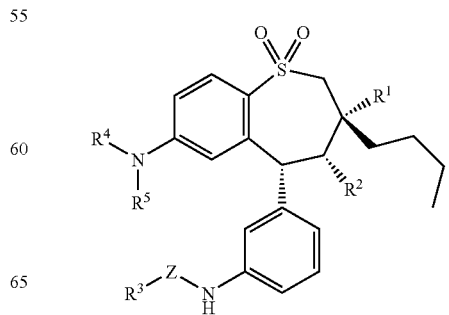

-continued

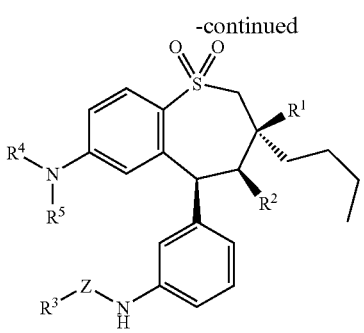

Sugar radicals are understood as meaning compounds which are derived from aldoses and ketoses having 3 to 7 carbon atoms and which can belong to the D or L series; these also include amino sugar, sugar alcohols or sugar acids. Examples which may be mentioned are glucose, mannose, fructose, galactose, ribose, erythrose, glyceraldehyde, sedoheptulose, glucosamine, galactosamine, glucuronic acid, galacturonic acid, gluconic acid, galactonic acid, mannonic acid, glucamine, 3-amino-1,2-propanediol, glucaric acid and galactaric acid.

Preferred sugar radicals are:

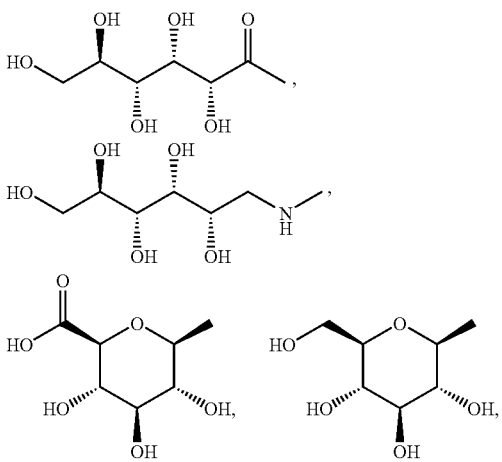

Particularly preferred sugar radicals are:

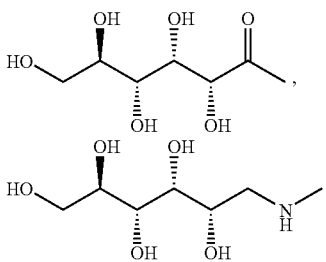

Disugars mean saccharides which consist of two sugar units. Di-, tri- or tetrasaccharides are formed by acetal-like bonding of 2 or more sugars. The bonds can in this case occur in the α or β form. Examples which may be mentioned are lactose, maltose and cellobiose.

If the sugar is substituted, the substitution preferably takes place with the hydrogen atom of an OH group of the sugar.

Possible protective groups for the hydroxyl groups of the sugars are preferably the following: benzyl, acetyl, benzoyl, pivaloyl, trityl, tert-butyldimethylsilyl, benzylidene, cyclohexylidene or isopropylidene protective groups. These protective groups are referred to herein as "sugar protective groups."

The invention furthermore relates to a process for the preparation of benzothiepine 1,1-dioxide derivatives of formula I:

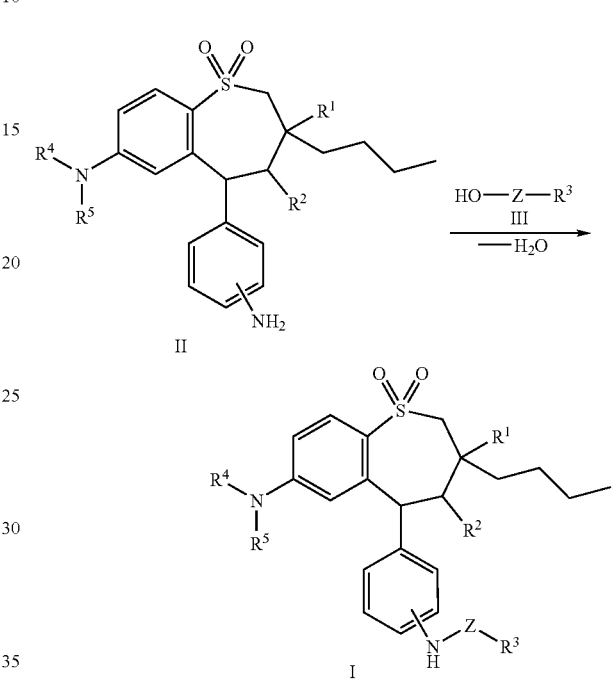

which comprises reacting an amine of formula II or a salt thereof, in which $R^1$, $R^2$, $R^4$ and $R^5$ have the meanings indicated for formula I, with a compound of formula III or a salt thereof, in which $R^3$ and Z have the meanings indicated for formula I, with elimination of water to give a compound of formula I and optionally converting the compound of formula I obtained into a physiologically tolerable salt or a physiologically functional derivative. If the radical $R^3$ is a monosugar radical, this radical can optionally also still be lengthened stepwise so as to give the disugar radical, trisugar radical or tetrasugar radical after bonding to the amine of formula II.

The following findings confirm the pharmacological efficacy of the compounds according to the invention.

The biological testing of the compounds according to the invention was carried out by determination of the $ED_{200}$ excretion. This testing investigates the action of the compounds according to the invention on the bile acid transport in the ileum and the fecal excretion of bile acids in the rat after oral administration twice daily. The diastereomer mixtures of the compounds were tested.

The test was carried out as follows:

1) Preparation of the Test and Reference Substances

The following recipe was used for the formulation of an aqueous solution:

the substances were dissolved in adequate volumes of an aqueous solution comprising Solutol (=polyethylene glycol 600 hydroxystearate; BASF, Ludwigshafen, Germany;

Batch No. 1763), so that a final concentration of 5% of Solutol is present in the aqueous solution. The solutions/suspensions were administered orally in a dose of 5 ml/kg.

2) Experimental Conditions

Male Wistar rats (Kastengrund, Hoechst AG, weight range 250–350 g) were kept in groups of 6 animals each and received a standard feed mixture (Altromin, Lage, Germany) from 10 days before the start of treatment (day 1) with a reversed day/night rhythm (4.00–16.00 dark, 16.00–4.00 light). Three days before the start of the experiment (day 0), the animals were divided into groups of 4 animals each.

TABLE 1

Division of the animals into treatment groups:

| Number of the group | Animal No./ Analysis No. | Test substance[1] (See Table 2) | Dose (mg/kg/d) |
|---|---|---|---|
| 1 | 1–4 | negative control | Vehicle |
| 2 | 5–8 | Test substance Dose 1 | 2 × 0.008 |
| 3 | 9–12 | Test substance Dose 2 | 2 × 0.02 |
| 4 | 13–16 | Test substance Dose 3 | 2 × 0.1 |
| 5 | 17–20 | Test substance Dose 4 | 2 × 0.5 |

[1] dissolved/suspended in 5% Solutol HS 15/0.4% starch mucilage

3) Experimental Course

After intravenous or subcutaneous administration of 5 µCi of $^{14}$C-taurocholate per rat (day 0), the vehicles or test substances were given at 7.00–8.00 and at 15.00–16.00 on the following day (day 1) (treatment for one day).

Stool samples for the analysis of C-taurocholate were taken every 24 hours directly after the administration of the morning dose. The feces were weighed, stored at −18° C. and later suspended in 100 ml of demineralized water and homogenized (Ultra Turrax, Janke & Kunkel, IKA-Werk). Aliquot parts (0.5 g) were weighed and combusted on combustion lids (Combusto Cones, Canberra Packard) in a combustion apparatus (Tri Carb® 307 combuster Canberra Packard GmbH, Frankfurt am Main, Germany). The resulting $^{14}CO_2$ was absorbed with Carbo-Sorb® (Canberra Packard). The following $^{14}$C radioactivity measurements were determined after addition of the scintillator (Perma-Fluor complete scintillation cocktail No. 6013187, Packard) to the samples with the aid of liquid scintillation counting (LSC). The fecal excretion of $^{14}$C-taurocholic acid was calculated as a cumulative and/or percentage residual radioactivity (see below).

4) Observations and Measurements

The fecal excretion of $^{14}$C-TCA was determined in combusted aliquot parts of the stool samples taken at 24-hour intervals, calculated as the "cumulative percentage" of the administered activity and expressed as a % of the residual activity (=remaining activity, i.e. administered activity minus the already excreted activity). For the calculation of the dose-response curves, the excretion of $^{14}$C taurocholic acid was expressed as a percentage proportion of the corresponding values of the control group (treated with vehicle). The $ED_{200}$, i.e. the dose which increases the fecal excretion of $^{14}$C taurocholic acid to 200% of the control group, is calculated from a sigmoid or linear dose-response curve by interpolation. The calculated $ED_{200}$ corresponds to a dose which doubles the fecal excretion of bile acids.

5) Results

Table 2 shows measurements of the $ED_{200}$ excretion.

TABLE 2

| Compounds from Example (diastereomer mixture) | $ED_{200}$ excretion (mg/kg/d) p.o. |
|---|---|
| 1 | 0.009 |
| 2 | 0.008 |
| 3 | 0.04 |
| 5 | 0.03 |
| 6 | 0.04 |
| 7 | 0.04 |
| 8 | 0.007 |
| 9 | 0.007 |
| 10 | 0.04 |
| 3 (pure structure 11a) | 0.008 |
| Comparison Examples | |
| 1 | 0.8 |
| 2 | 1.0 |
| 3 | 0.9 |

6) Discussion

It can be inferred from the measured data that the compounds of formula I according to the invention are more active by a factor of 20 to 100 compared with the compounds previously known.

The following Examples serve to illustrate the invention in greater detail without restricting the scope of the invention to products and embodiments described in the Examples.

EXAMPLE 1

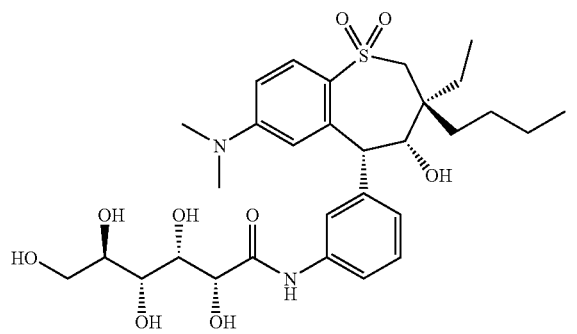

4a

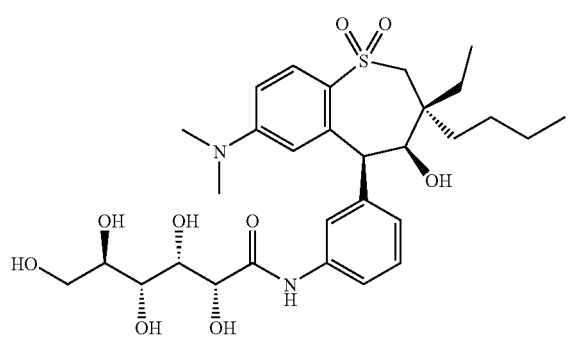

4b $C_{30}H_{44}N_2O_9S$ (608.76). MS (M+H)$^+$=609.3

EXAMPLE 2
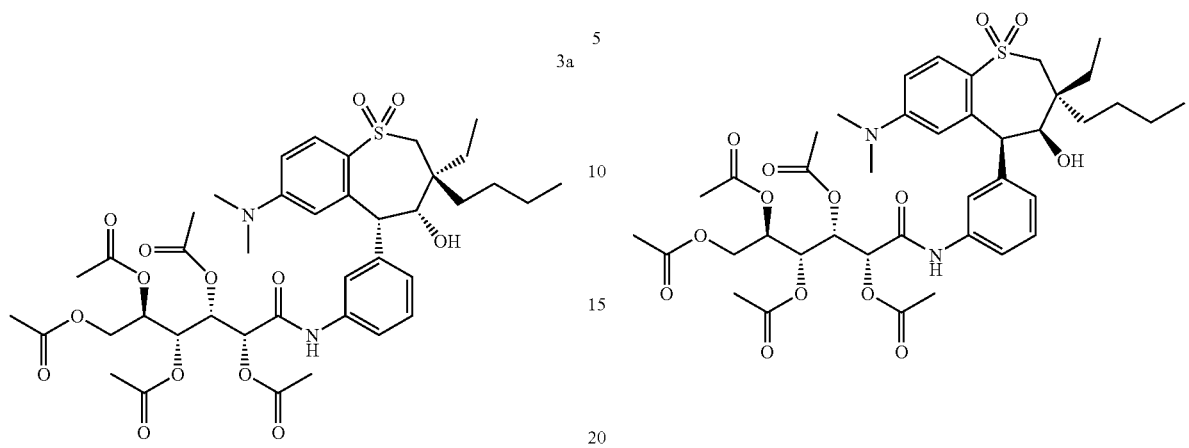
$C_{40}H_{54}N_2O_{14}S$ (818.40). MS (M+H)$^+$=819.3
EXAMPLE 3
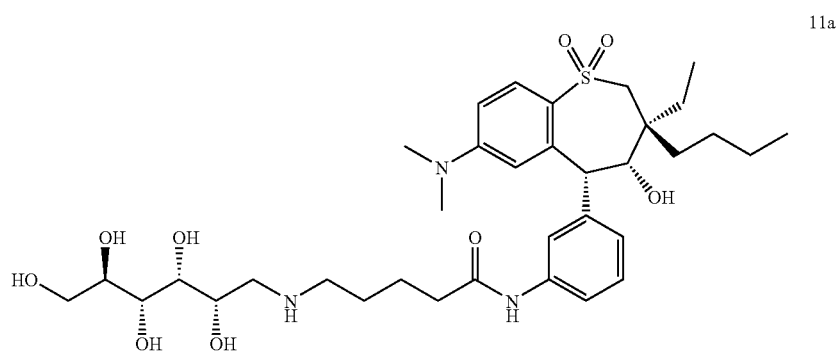
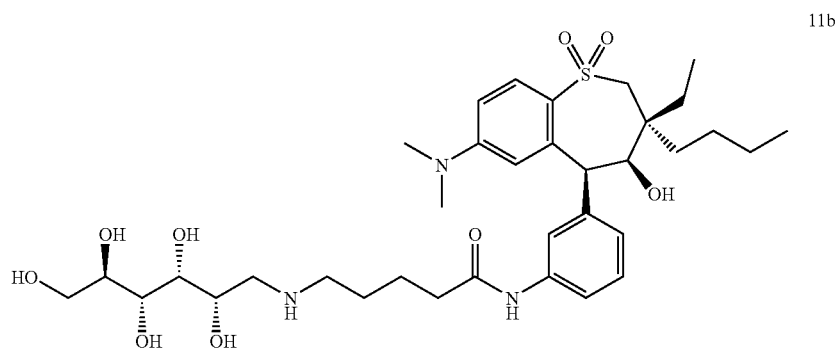
$C_{35}H_{55}N_3O_9S$ (693.91). MS (M+H)$^+$=694.4

EXAMPLE 4
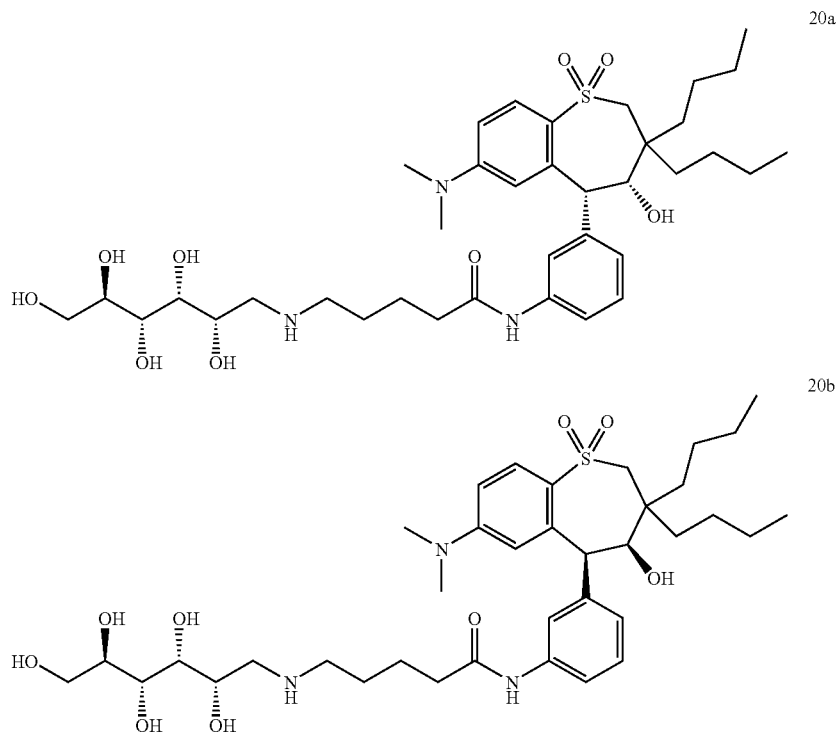
$C_{37}H_{59}N_3O_9S$ (721.96). MS (M+H)$^+$=722.3
EXAMPLE 5
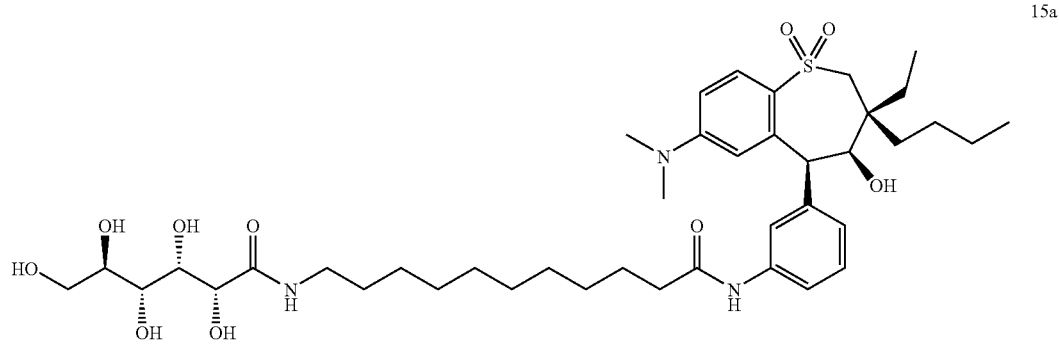
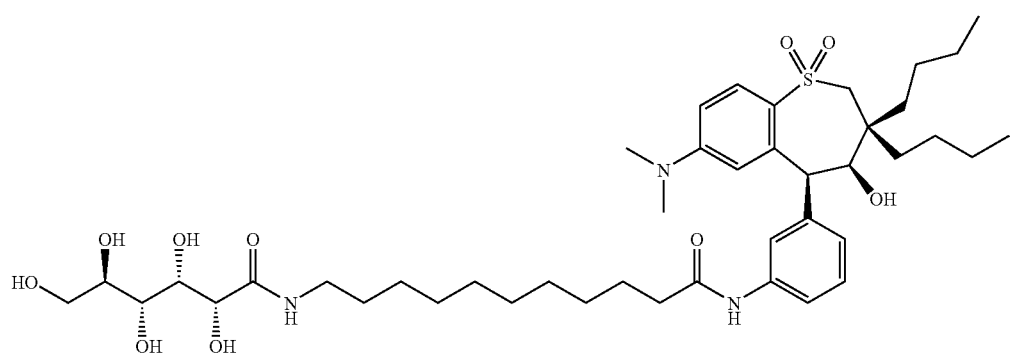
$C_{41}H_{65}N_3O_{10}S$ (792.05). MS (M+H)$^+$=792.5

EXAMPLE 6
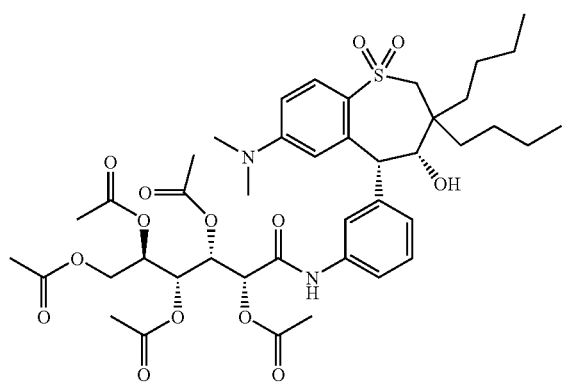
6a
6b
$C_{42}H_{58}N_2O_{14}S$ (846.97). MS (M+H)$^+$=847.4
EXAMPLE 7
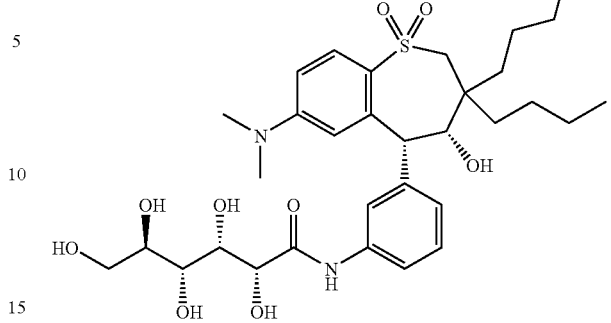
7a
7b
$C_{32}H_{48}N_2O_9S$ (636.80). MS (M+H)$^+$=637.4
EXAMPLE 8
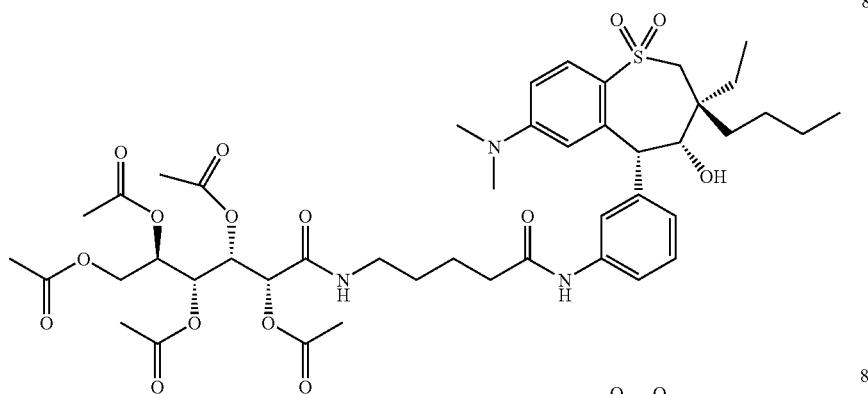
8a
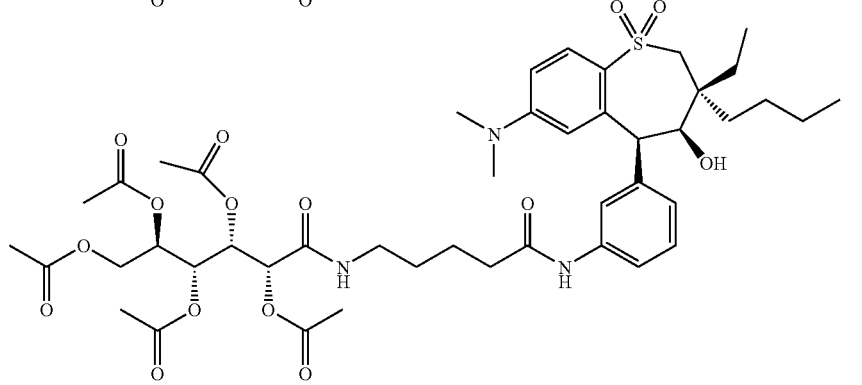
8b
$C_{45}H_{63}N_3O_{15}S$ (918.06). MS (M+H)$^+$=918.6

EXAMPLE 9
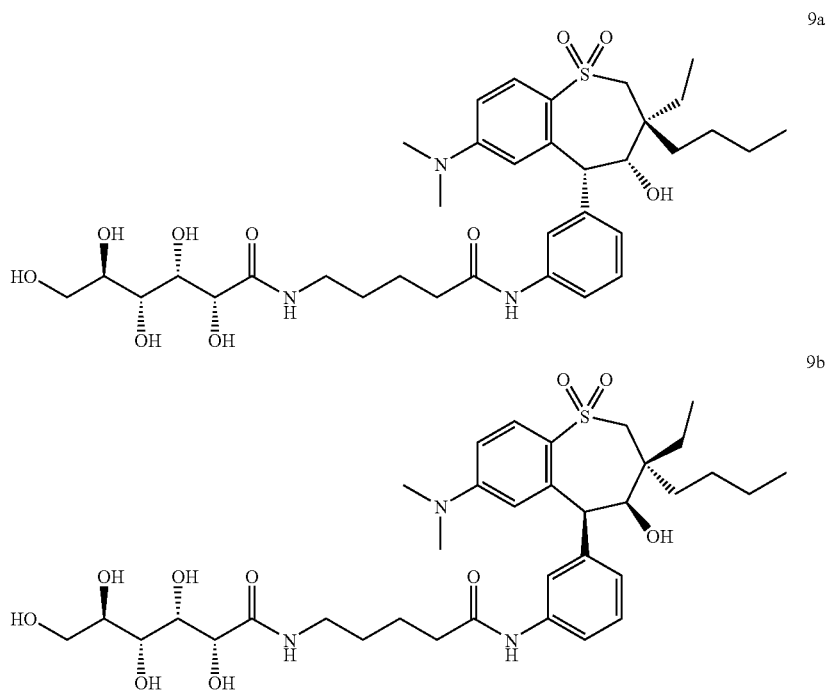
$C_{35}H_{53}N_3O_{10}S$ (707.88). MS (M+H)$^+$=708.4
EXAMPLE 10
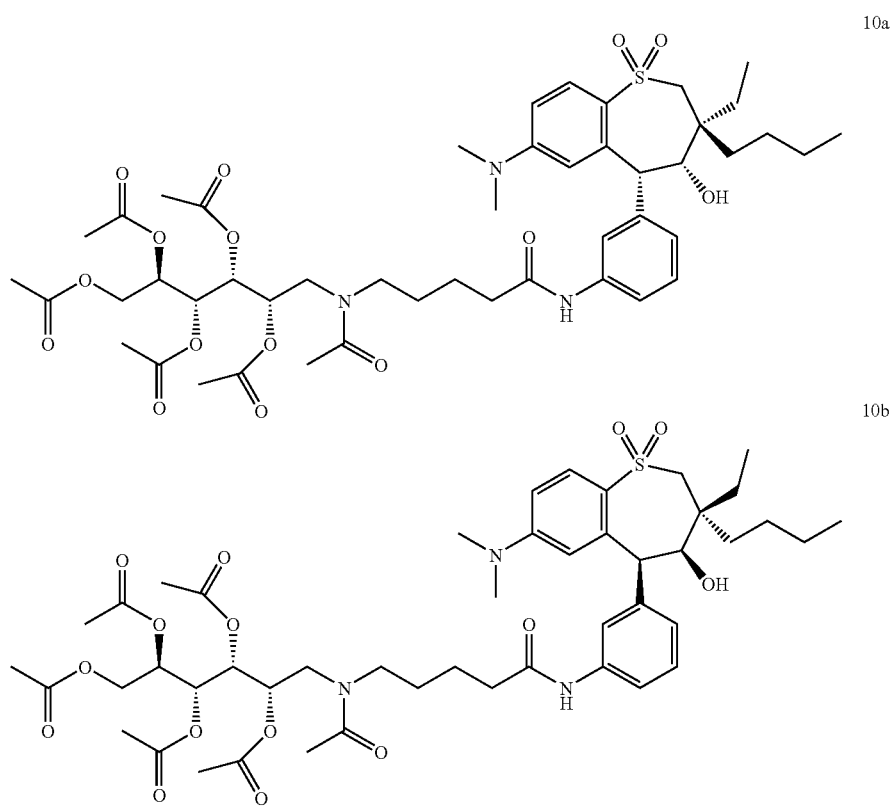
$C_{47}H_{67}N_3O_{15}S$ (946.12). MS (M+H)$^+$=946.5

Comparison Examples from PCT/US97/04076:
COMPARISON EXAMPLE 1
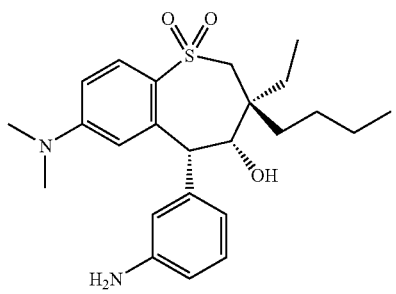
1a
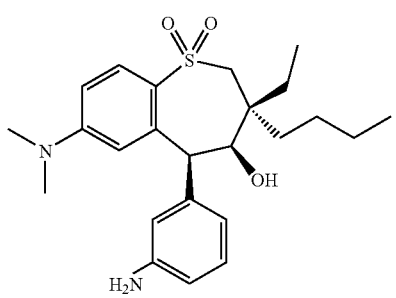
1b
COMPARISON EXAMPLE 2
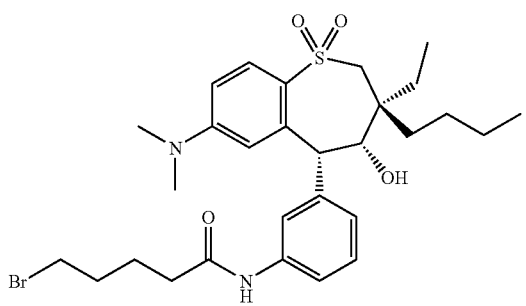
30a
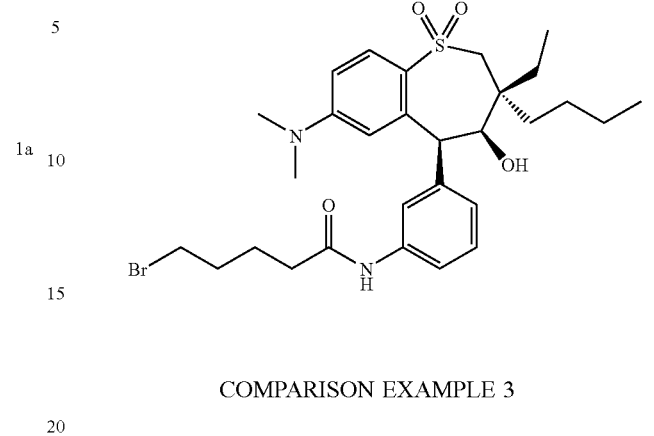
30b
COMPARISON EXAMPLE 3
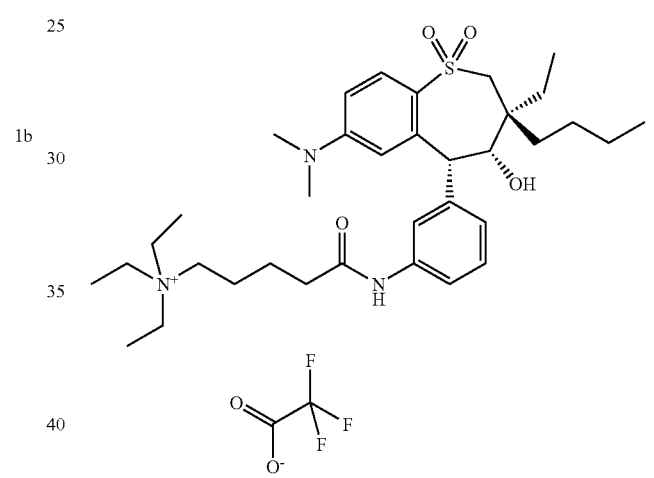
22a
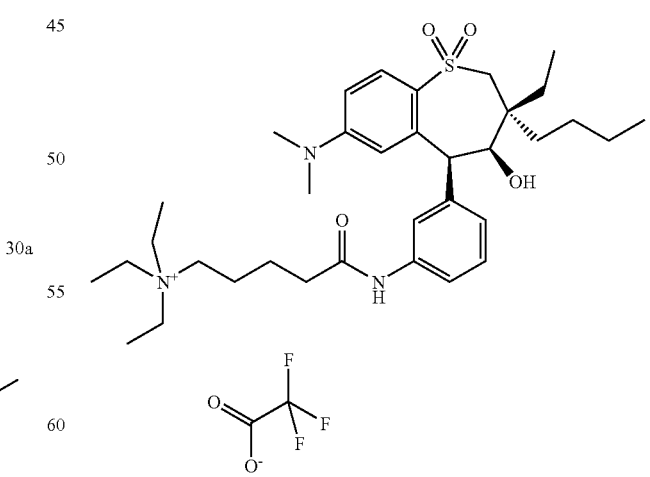
22b
The Examples and Comparison Examples were prepared as follows (in the preparations only the synthesis of the "a" diastereomers is shown):

Reaction scheme 1
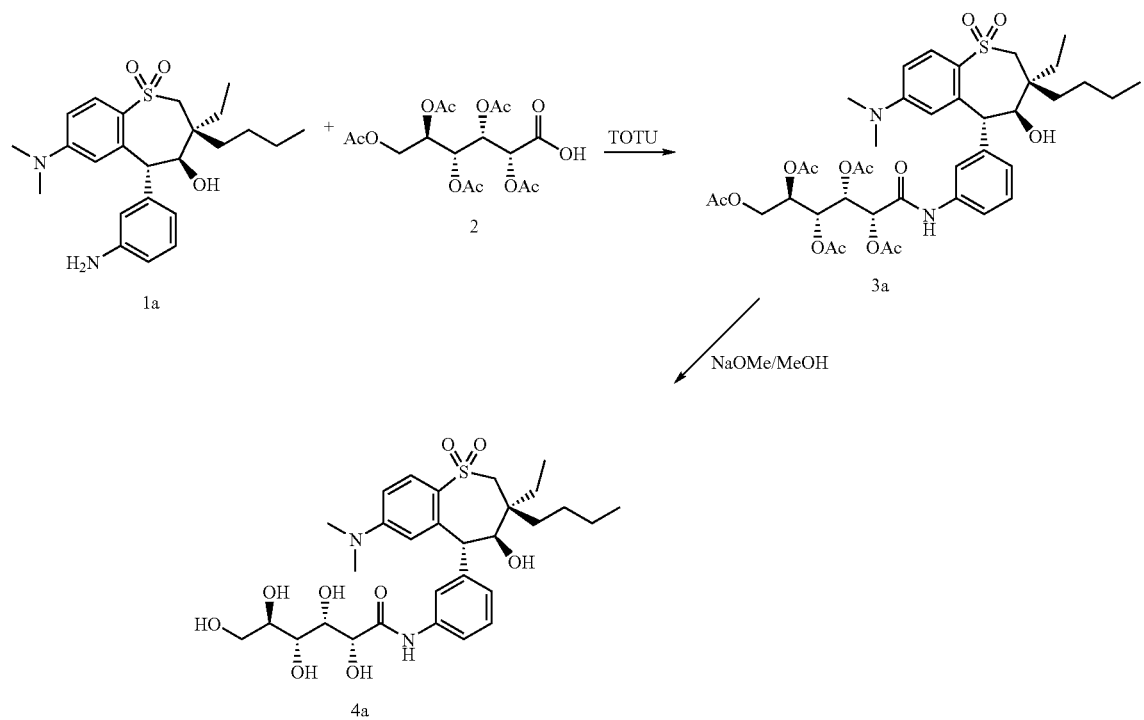
Reaction scheme 2
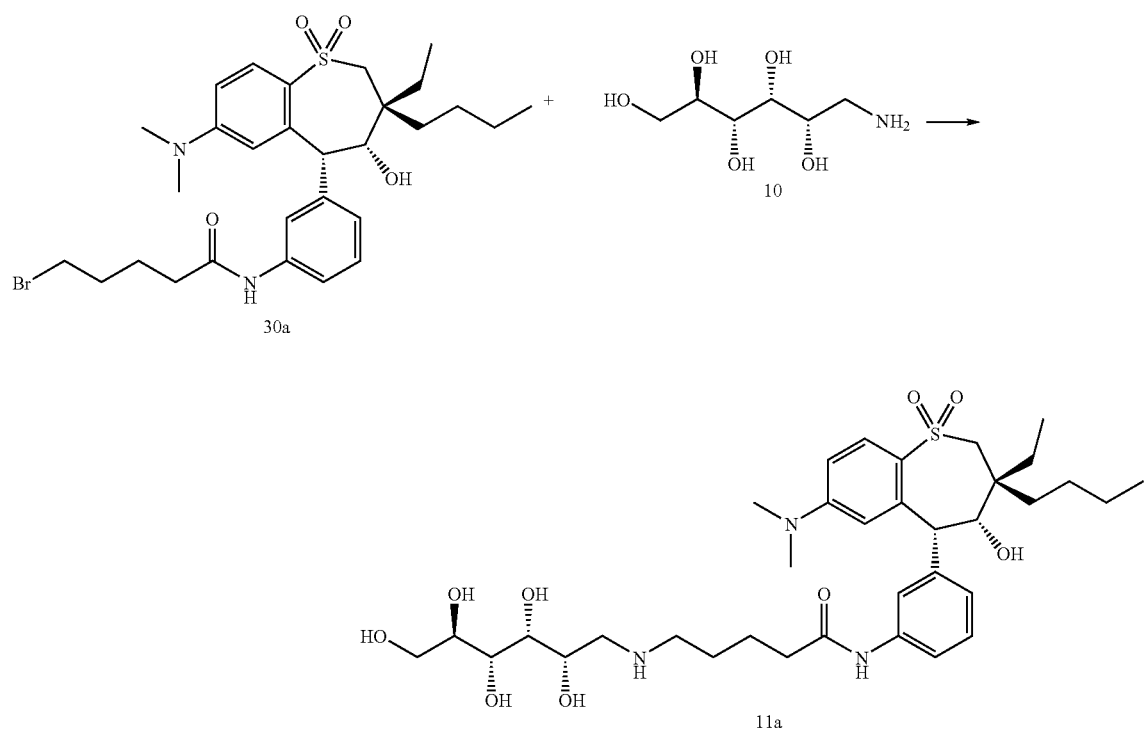

Reaction scheme 3

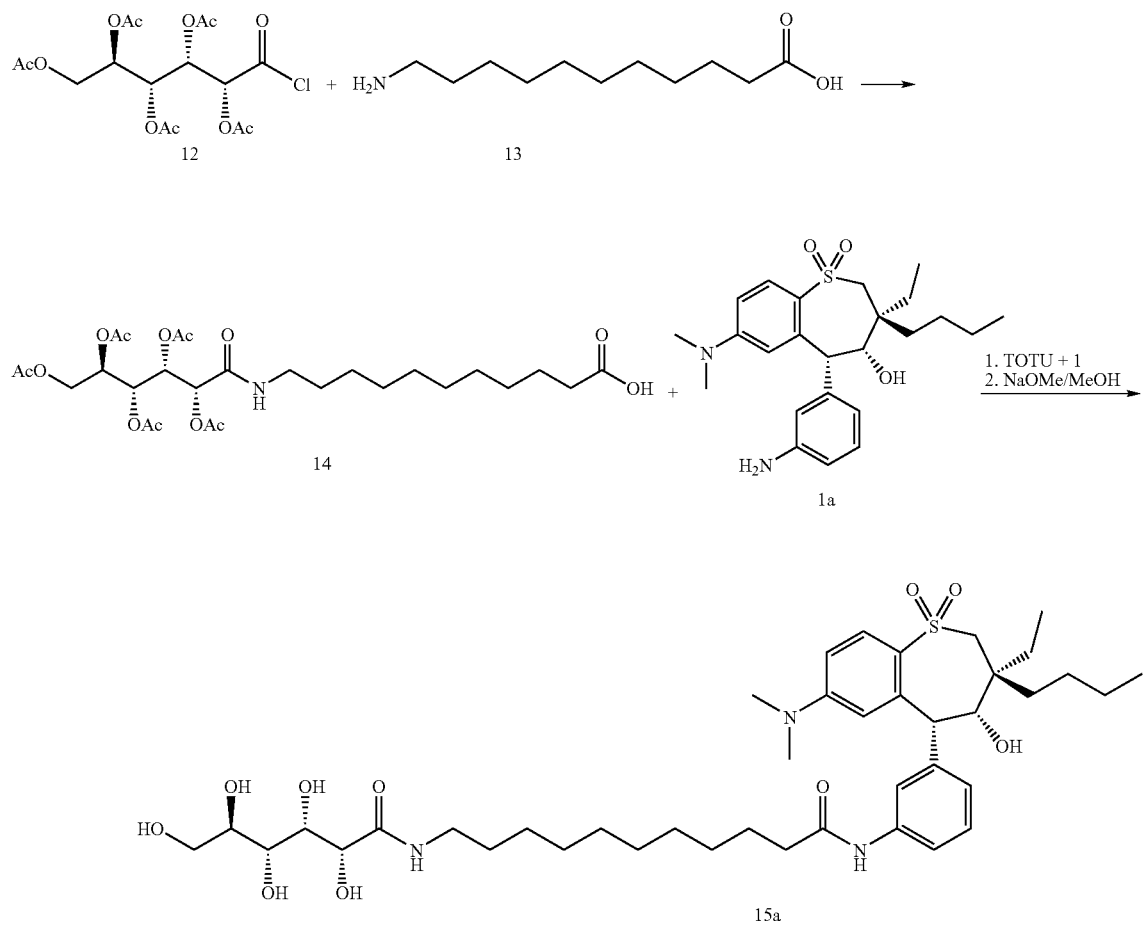

Synthesis of Compound 3 as a Diastereomer Mixture:

300 mg (0.69 mmol) of 1a/b (preparation analogous to PCT/US97/04076) and 700 mg (1.7 mmol) of penta-O-acetyl-D-gluconic acid (Charles E. Braun and Clinton D. Cook, 5 ORG. SYNTH. 887 (1973), the relevant disclosure of which is incorporated by reference herein) are dissolved in 10 ml of DMF (dimethylformamide). 700 mg (2.1 mmol) of TOTU (Fluka), 250 mg (1.7 mmol) of oxime (ethyl hydroxy-iminocyanoacetate; Fluka) and 0.7 ml (5.5 mmol) of NEM (4-ethylmorpholine) are added successively. After one hour at room temperature, the mixture is diluted with 100 ml of ethyl acetate and washed three times with water. The organic phase is dried over $MgSO_4$, filtered and concentrated. The residue is purified by means of flash chromatography (ethyl acetate/n-heptane 2:1) and 502 mg (88%) of 3a/b are obtained as an amorphous solid. TLC (ethyl acetate/n-heptane 2:1) $R_f$= 0.3. The product 3a/b has the same retention as the starting material 1a/b, but stains differently with 2 M sulfuric acid.

$C_{40}H_{54}N_2O_{14}S$ (818.40). MS $(M+H)^+$=819.3.

Synthesis of Compound 4 as a Diastereomer Mixture:

455 mg (0.55 mmol) of 3a/b are dissolved in 20 ml of methanol. After addition of 0.3 ml of a methanolic 1 M sodium methoxide solution, the mixture is allowed to stand at room temperature for one hour. It is then neutralized with methanolic HCl solution and concentrated. The residue is purified using flash chromatography (methylene chloride/methanol/conc. ammonia 30/5/1) and 280 mg (83%) of 4a/b are obtained as an amorphous solid. TLC (methylene chloride/methanol/conc. ammonia 30/5/1). $R_f$=0.2.

$C_{30}H_{44}N_2O_9S$ (608.76). MS $(M+H)^+$=609.3.

Synthesis of Compound 11 as a Diastereomer Mixture:

77 mg (0.013 mmol) of 30a/b (preparation analogous to PCT/US97/04076) are dissolved in 4 ml of DMF. After addition of 150 mg (0.082 mmol) of 10 (glucamine, Fluka), the mixture is heated at 80° C. for two hours. It is then diluted with 50 ml of ethyl acetate and washed three times with water. The organic phase is dried over $MgSO_4$, filtered and concentrated. The residue is purified by means of flash chromatography (methylene chloride/methanol/conc. ammonia 30/5/1) and 55 mg (61%) of 11a/b are obtained as an amorphous solid. TLC (methylene chloride/methanol/conc. ammonia 30/511). $R_f$=0.3.

$C_{35}H_{55}N_3O_9S$ (693.91). MS $(M+H)^+$=694.4.

Synthesis of Compound 14:

8.0 g (18.8 mmol) of 12 (penta-O-acetyl-D-gluconic acid chloride; Org. Synth. Volume 5, 887) are added to a suspension of 8.0 g (40 mmol) of 13 (Fluka) in 150 ml of anhydrous DMF. This suspension is vigorously stirred at room temperature for 20 hours. 500 ml of ethyl acetate and 200 ml of water are then added. The aqueous phase is extracted again with 250 ml of ethyl acetate. The combined organic phase is washed three times with sodium chloride solution, dried over MgSO$_4$, filtered and concentrated. Yield 9.5 g (86%) of 14 as a colorless oil. TLC (methylene chloride/methanol/conc. ammonia 30/10/3). R$_f$=0.8.

C$_{27}$H$_{43}$NO$_{13}$ (589.64). MS (M+H)$^+$=590.4.

Synthesis of Compound 15 as a Diastereomer Mixture:

200 mg (0.34 mmol) of 14, 78 mg (0.18 mmol) of 1a/b, 240 mg of TOTU, 80 mg of oxime and 0.3 ml of NEM are reacted in 4 ml of DMF analogously to the procedure for compound 4. After flash chromatography (methylene chloride/methanol/conc. ammonia 30/5/1), 47 mg (33%, over two steps) of 15a/b are obtained as an amorphous solid. TLC (methylene chloride/methanol/conc. ammonia 30/5/1). R$_f$=0.2.

C$_{41}$H$_{65}$N$_3$O$_{10}$S (792.05). MS (M+H)$^+$=792.5.

The invention may be embodied in other specific forms and those skilled in the art will recognize that various changes and modifications can be made without departing from the spirit or essential characteristics thereof. The present embodiment is, therefore, considered in all respects as illustrative and not restrictive. Embodiments are measured by the scope of the appended claims rather than by the foregoing description, and all changes which come within the meaning and range of equivalency of the claims are therefore intended to be embraced therein.

We claim:

1. A coated pharmaceutical composition comprising at least one compound of formula I

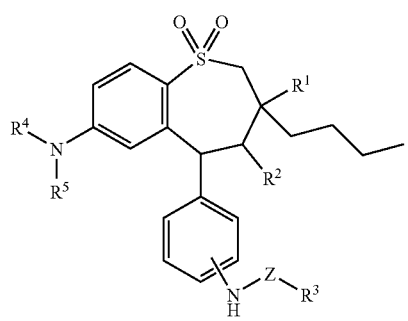

in which

R$^1$ is methyl, ethyl, propyl, or butyl;
R$^2$ is H, OH, NH$_2$, or NH—(C$_1$–C$_6$)-alkyl;
R$^3$ is a sugar radical, a disugar radical, a trisugar radical, or a tetrasugar radical, wherein said radicals are optionally mono- or polysubstituted by a sugar protective group;
R$^4$ is methyl, ethyl, propyl, or butyl;
R$^5$ is methyl, ethyl, propyl, or butyl;
Z is —(C═O)$_n$—(C$_0$–C$_{16}$)-alkyl, —(C═O)$_n$—(C$_0$–C$_{16}$)-alkyl-NH—, —(C═O)$_n$—(C$_0$–C$_{16}$)-alkyl-O—, —(C═O)$_n$—(C$_1$–C$_{16}$)-alkyl-(C═O)$_m$, or a covalent bond;
n is 0 or 1;
m is 0 or 1;
or a pharmaceutically tolerable salt thereof, or a physiologically functional derivative thereof,
and at least one pharmacologically tolerable excipient.

2. A coated pharmaceutical composition as claimed in claim 1, wherein in the formula I:
R$^1$ is ethyl, propyl, or butyl;
R$^2$ is H, OH, NH$_2$, or NH—(C$_1$–C$_{16}$)-alkyl;
R$^3$ is a sugar radical or disugar radical, wherein said radicals are optionally mono- or polysubstituted by a sugar protective group;
R$^4$ is methyl, ethyl, propyl, or butyl;
R$^5$ is methyl, ethyl, propyl, or butyl;
Z is —(C═O)$_n$—(C$_0$–C$_{16}$)-alkyl-, —(C═O)$_n$—(C$_0$–C$_{16}$)alkyl-NH—, —(C═O)$_n$—(C$_0$–C$_{16}$)-alkyl-O—, —(C═O)$_n$—(C$_1$–C$_{16}$)-alkyl-(C═O)$_m$, or a covalent bond;
n is 0 or 1; and
m is 0 or 1.

3. A coated pharmaceutical composition as claimed in claim 1, wherein in the formula I:
R$^1$ is ethyl or butyl;
R$^2$ is OH;
R$^3$ is a sugar radical, wherein the sugar radical is optionally mono- or polysubstituted by a sugar protective group;
R$^4$ is methyl;
R$^5$ is methyl; and
Z is —(C═O)–(C$_0$–C$_4$)-alkyl or a covalent bond.

4. A coated pharmaceutical composition as claimed in claim 1, wherein the composition comprises a compound of the following structure:

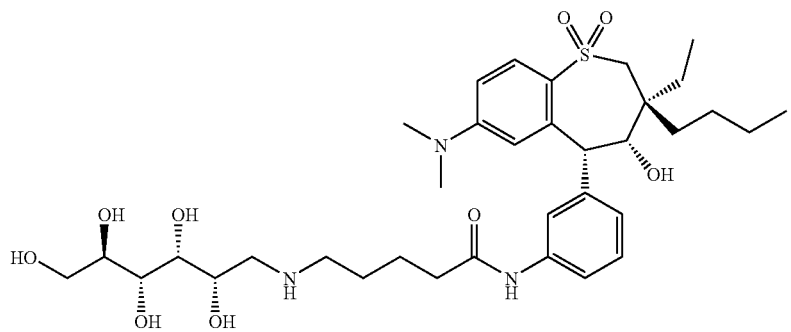

or a pharmaceutically tolerable salt thereof.

5. A coated pharmaceutical composition as claimed in claim 1, wherein the composition comprises a compound of the following structure:

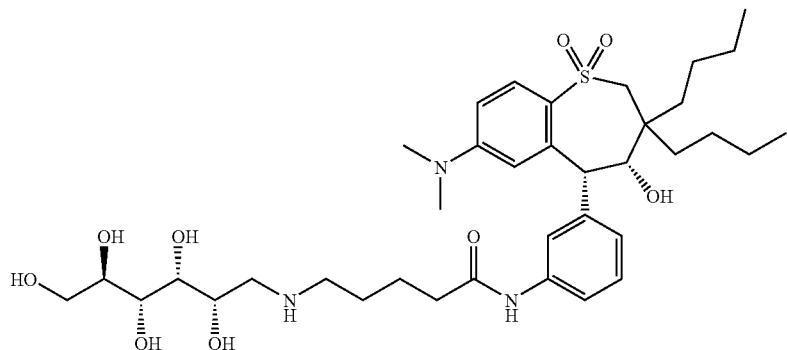

or a pharmaceutically tolerable salt thereof.

6. A coated pharmaceutical composition as claimed in claim 1, wherein the composition is a delayed-release composition.

7. A coated pharmaceutical composition as claimed in claim 1, wherein the composition is acid-resistant.

8. A coated pharmaceutical composition as claimed in claim 1, wherein the composition is an enteric composition.

9. A coated pharmaceutical composition as claimed in claim 1, wherein the coating comprises cellulose acetate phthalate, polyvinyl acetate phthalate, hydroxypropylmethylcellulose phthalate or one or more anionic polymers of methacrylic acid and methyl methacrylate.

10. A coated pharmaceutical composition as claimed in claim 8, wherein the coating comprises cellulose acetate phthalate, polyvinyl acetate phthalate, hydroxypropylmethylcellulose phthalate or one or more anionic polymers of methacrylic acid and methyl methacrylate.

* * * * *